(12) United States Patent
Eshel et al.

(10) Patent No.: US 10,188,786 B2
(45) Date of Patent: Jan. 29, 2019

(54) METHOD AND SYSTEM FOR TREATING BLADDER CONDITIONS

(75) Inventors: Uzi Eshel, Tel-Aviv (IL); Jacob Lazarovitz, Hod-HaSharon (IL)

(73) Assignee: Elmedical Ltd., Hod-HaSharon (IL)

( * ) Notice: Subject to any disclaimer, the term of this patent is extended or adjusted under 35 U.S.C. 154(b) by 939 days.

(21) Appl. No.: 13/181,569

(22) Filed: Jul. 13, 2011

(65) Prior Publication Data

US 2012/0016335 A1 Jan. 19, 2012

Related U.S. Application Data

(60) Provisional application No. 61/399,479, filed on Jul. 14, 2010.

(51) Int. Cl.
*A61M 3/02* (2006.01)

(52) U.S. Cl.
CPC ........ *A61M 3/0295* (2013.01); *A61M 3/0283* (2013.01); *A61M 2205/3331* (2013.01); *A61M 2205/3368* (2013.01); *A61M 2205/3626* (2013.01)

(58) Field of Classification Search
CPC .. A61M 2210/1085; A61M 2210/1078; A61M 16/0463; A61M 2205/3331; A61M 2205/3368; A61M 2205/36; A61M 2205/33; A61M 25/00; A61M 25/04; A61M 25/10; A61M 25/1002; A61M 29/02; A61M 3/0283; A61M 3/0295; A61M 2205/3626; A61M 5/44; A61M 1/106; A61B 2018/00577; A61B 5/01; A61B 5/4836; A61B 2018/044; A61B 18/14; A61B 2018/00517; A61F 7/123; A61F 2007/0054; A61F 2007/0095; A61F 7/12

USPC ........... 604/500, 113, 517, 544; 600/29, 561

See application file for complete search history.

(56) References Cited

U.S. PATENT DOCUMENTS

| | | | | |
|---|---|---|---|---|
| 4,946,440 A * | 8/1990 | Hall | ....................... | A61B 18/08 600/569 |
| 5,460,628 A * | 10/1995 | Neuwirth | ............... | A61B 18/08 606/27 |
| 5,549,559 A * | 8/1996 | Eshel | ............................ | 604/113 |
| 6,648,906 B2 * | 11/2003 | Lasheras | .................. | A61F 7/12 604/27 |
| 6,849,063 B1 * | 2/2005 | Eshel et al. | .................... | 604/113 |
| 2003/0229263 A1 * | 12/2003 | Connors | ................ | A61B 5/205 600/29 |
| 2005/0054994 A1 * | 3/2005 | Cioanta | .............. | A61B 10/0045 604/317 |
| 2007/0142773 A1 * | 6/2007 | Rosiello et al. | ............. | 604/113 |
| 2008/0172041 A1 * | 7/2008 | Shehata | ........................ | 604/544 |
| 2010/0111914 A1 * | 5/2010 | Zhang | .................... | A61K 35/22 424/93.21 |

* cited by examiner

*Primary Examiner* — Brandy S Lee

(57) ABSTRACT

A method of treating a bladder condition is provided. The method is effected by circulating a volume of heated fluid through a urinary bladder of a subject in need and gradually increasing the volume of fluid up to a predetermined fluid volume and or pressure.

7 Claims, 1 Drawing Sheet

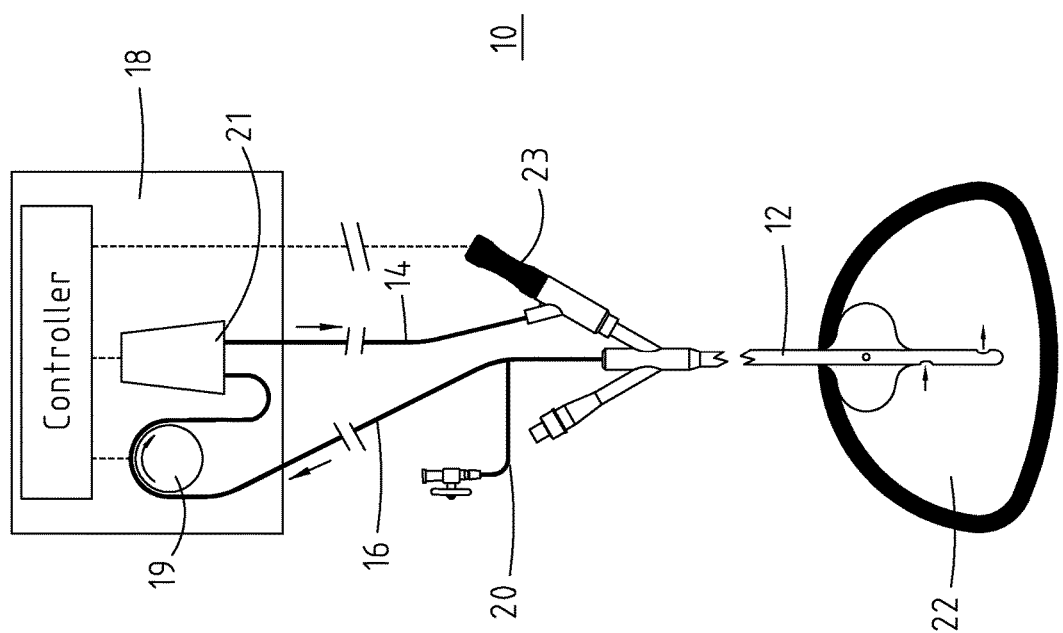

METHOD AND SYSTEM FOR TREATING BLADDER CONDITIONS

RELATED APPLICATION

This application claims the benefit of priority of U.S. Provisional Patent Application No. 61/399,479 filed on Jul. 14, 2010. The contents of the above application is incorporated herein by reference.

FIELD AND BACKGROUND OF THE INVENTION

The present invention relates to a system and method for treating bladder conditions such as overactive bladder (OAB) and interstitial cystitis/bladder pain syndrome (IC/BPS).

OAB is a condition characterized by sudden, involuntary contractions of the muscle in the wall of the urinary bladder (detrusor muscle). Overactive bladder causes a sudden and unstoppable need to urinate (urinary urgency), even though the bladder may only contain a small amount of urine. OAB is distinct from stress urinary incontinence, but when they occur together is usually known as mixed incontinence.

The etiology of OAB is unclear, there may be multiple possible causes. Since OAB is often associated with detrusor overactivity, treatments are usually synonymous with treatments for detrusor overactivity.

Treatment for OAB includes lifestyle modification (fluid restriction, avoidance of caffeine), bladder retraining by scheduled urination, antimuscarinic drugs (darifenacin, hyoscyamine, oxybutynin, tolterodine, solifenacin, trospium), and various devices (Urgent PC Neuromodulation System, InterStim). Intravesical botulinum toxin A is also used in some intractable cases, although not with formal FDA approval.

Hydrodistention of the bladder is one of the oldest treatments for interstitial cystitis/bladder pain syndrome and has recently been applied to overactive bladder cases with modest success. Hydrodistention is a procedure in which the bladder is stretched using water or a physiological fluid delivered into the bladder under pressure of up to 90-100 cm of water.

In OAB and IC/BPS cases, this procedure provides short-term relief from symptoms possibly by affecting unmyelinated C-fibers in the bladder and thereby producing local deafferentation (Dmochowski Rev Urol. 2002; 4 (Suppl 4): S19-S27).

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 illustrates a system which can be used for treating bladder conditions according to the teachings of the present invention.

SUMMARY OF THE INVENTION

According to one aspect of the present invention there is provided a method of treating a bladder condition comprising: (a) circulating a volume of fluid maintained at a temperature of 40-48° C. through a urinary bladder of a subject in need; and (b) gradually increasing the volume of fluid up to a predetermined fluid volume and/or pressure.

According to further features in preferred embodiments of the invention described below, the bladder condition is overactive bladder.

According to still further features in the described preferred embodiments the bladder condition is interstitial cystitis/bladder pain syndrome.

According to still further features in the described preferred embodiments the predetermined fluid pressure is 30-60 cm of water.

According to still further features in the described preferred embodiments the circulating is effected using a closed loop system.

According to still further features in the described preferred embodiments (b) is effected by suctioning fluid into the closed loop system.

According to still further features in the described preferred embodiments the suctioning is effected while the fluid is circulating through the closed loop system.

According to still further features in the described preferred embodiments the predetermined fluid volume is in a range of 200 to 800 ml.

According to still further features in the described preferred embodiments the predetermined fluid pressure is in a range of 30 to 60 cm of water.

The present invention successfully addresses the shortcomings of the presently known configurations by employing a closed loop fluid circulating system capable of effectively circulating heated and pressurized fluid through the bladder.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

DESCRIPTION OF THE PREFERRED EMBODIMENTS

The present invention relates to an approach which can be used to treat bladder condition. Specifically, the present invention can be used to treat overactive bladder and interstitial cystitis/bladder pain syndrome.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting. Although hydrodistention of the bladder appears to be a promising treatment approach, it can lead to complications such as bladder infections, transient hematuria, bladder wall tears or perforations and tissue necrosis.

In efforts of overcoming the limitations of presently used hydrodistention approaches, the present inventors have devised a novel treatment approach which utilizes closed irrigation of the bladder with heated fluid under lower pressures than that used in conventional hydrodistension.

The urinary bladder usually holds 300-350 mL of urine; a full adult bladder can hold about 500-1000 mL of urine, 15 times its empty volume. As urine accumulates, the wall of the bladder thins as it stretches, allowing the bladder to store larger amounts of urine without a significant rise in internal pressure. Such behavior of the bladder is like a balloon which expands its volume with no pressure rise.

The desire to urinate usually starts when the bladder reaches around 125% of its working volume. At this stage it is easy for the subject, if desired, to resist the urge to urinate. As the bladder continues to fill, the desire to urinate becomes stronger and harder to ignore. Eventually, the bladder will fill to the point where the urge to urinate becomes overwhelming, and the subject will no longer be able to ignore it. The bladder working volume is different between subjects and in OAB and IC/BPS patients tends to be lower than the working volume of healthy subjects.

Heat combined with mild and controlled bladder distension in a procedure termed herein as bladder thermal distention (BTD) relaxes the bladder muscle beyond its resting state during the filling phase, allowing bladder accommodation of even larger volumes of fluid (500 ml of fluid and more) without a significant rise in internal pressure (e.g. 40 cm of water). Incrementally filling the bladder with large volumes of heated fluid (at 40-48° C.) trains the bladder and increases its capacity without subjecting the bladder wall to the high pressures used in conventional hydrodistension (80-100 cm of water in the OR under anesthesia). This bladder training can increase the working volume of the bladder hence delaying the sense of urgency to urinate of a patient as described above. Without being bound to a theory, the present inventors also propose that BTD down regulates bladder innervation and thus enables further bladder wall stretching without activating the desire to urinate.

Thus according to one aspect of the present invention there is provided a method of treating a bladder condition. As used herein, the phrase "bladder condition" refers to any disorder or condition that originates in, or affects, the bladder. Examples include overactive bladder (OAB), interstitial cystitis/bladder pain syndrome (IC/BPS), pelvic pain syndrome (PPS), chronic pelvic pain syndrome (CPPS), mixed urgency, stress urinary incontinence, nocturnal eneuresis and diurinal eneuresis.

The present method is effected by circulating a volume of heated fluid through the urinary bladder of a subject and gradually increasing the volume of fluid up to a predetermined fluid volume and or pressure.

The fluid is preferably heated to 40-48° C. and the volume gradually increased (in increments of, for example, 50 ml at a rate of 30 to 100 ml per minute) to a final volume which reaches an intra-bladder pressure of no more than 60 cm of water.

By gradually increasing the volume of circulated fluid while concomitantly heating it, the present approach increases the volume of circulating fluid while maintaining a steady temperature thereby enabling a more effective, as well as a more gradual expansion of the bladder wall to a desired bladder volume/capacity endpoint.

The body adjusts to temperature elevation by clearing out excessive heat in order to maintain homeostasis. As such, heated fluid administered into the bladder will cool off to body temperature in a short time.

The present inventor suggests that in order to maintain elevated temperatures in the bladder, heated fluid must be circulated therethrough continuously (thus also achieving uniform heating). Although maintaining elevated temperatures in the bladder can also be effected by placing a heat source within the bladder and continuously energizing it (and, in the same time, utilize a stirring mechanism in order to achieve uniform heating), such an approach is complicated and costly to execute, and as such less preferred.

A recent study (Poster Presentation #779 by Zhonghong Guan et al presented in the EAU Meeting 2010) reported a linear correlation between voided volume and the sensation of urgency in subjects with overactive bladder (OAB), indicating that, at least for some patients, increased bladder volume during the filling phase may trigger urgency. The authors concluded that an increased bladder volume during the filling phase might, in part, be responsible for triggering urgency and that this supports the hypothesis that antimuscarinics reduce urgency, at least in part and in some patients, by increasing bladder capacity and thus by increasing the urgency sensation threshold.

Without being bound to a theory, the present inventors propose that circulating heated fluid while increasing the intra-bladder volume and pressure can be used to gradually increase bladder capacity and ameliorate symptoms without causing the complications of prior art approaches.

A subject suffering from OAB or IC/BPS can be treated using the present approach as follows.

The bladder is emptied using a catheter and approximately 150 ml of fluid containing saline and an anesthetic (e.g. 30 ml of an anesthetic agent+120 ml of saline or less in case of small capacity bladder) are injected into the bladder through the catheter. The fluid is circulated through the bladder using a closed system which includes a peristaltic pump and concomitantly heated to 40-48° C. using a fluid heater mounted over fluid conduits connected to the catheter. Irrigation is maintained for 50-60 minutes under heated circulation. Over the first 15-20 minutes, the 150 ml fluid solution is circulated with heating at about 44-45° C. (reached in about 5-10 min). Over the next 30-35 minutes, the volume of fluid is slowly and gradually increased in 50 ml saline increments by using a 50 ml syringe to inject the fluid (saline) into the closed loop system through a dedicated port. Over this phase of 30-35 minutes the irrigation temperature can be fixed or variable within the range of 40-48° C. The patient is continuously monitored for tolerance, which will be scored (and recorded) on Urinary Sensation Scale of 1 to 5 points (urgency scale). If needed, bladder volume can be reduced by draining through the dedicated port (using a syringe) in accordance to patient's tolerance.

Following 50 minutes of treatment, the bladder content (including the produced urine) is evacuated and measured using the 50 ml syringe (while trying, to the end of evacuation, to avoid sudden bladder collapse under vacuum). Immediately after emptying the bladder and before removing the catheter, another 30 ml of the anesthetic (and/or a medication such as Heparin) is injected through the catheter into the bladder to increase post procedure tolerance of the patient. The above described procedure is repeated several times over the course of several weeks or months until a desired bladder capacity is reached. A typical treatment regimen can include two to four procedures, two weeks to two months apart, followed by "maintenance" procedures, one to four months apart. Treatment endpoint (max bladder volume/capacity) depends on the patient's tolerance but is typically determined by a treating physician according to the initial bladder volume. When performing a series of bladder thermal distension procedures, bladder volume during procedures will increase gradually from procedure to procedure as bladder capacity improves.

For baseline evaluation and follow up evaluations the "standard" or "concise" battery of tests, voiding diaries (one day or three days) are employed.

The present approach can be effected using any catheter system capable of closed loop irrigation of the urinary bladder with heated fluid. An example of one system which can be used with the present approach is provided in FIG. 1.

System 10 includes a catheter 12 designed for insertion into a urinary bladder 22. Catheter 12 is preferably a three way catheter (one fluid conduit to inflate a positioning balloon and other two fluid conduits for the heated circulation) fabricated from a biocompatible material such as silicone and has the following dimensions length—20 to 40 cm, external diameter 5 to 6 mm and wall thicknesses 0.4 to 1.0 mm.

Catheter 12 includes fluid conduits which are connectable to fluid inlet line 14 (having an internal diameter of 2 to 4 mm) and fluid outlet line 16 (having an internal diameter of 2 to 4 mm). Lines 14 and 16 are interconnected and run through a controller 18 which includes a pump (e.g. peristaltic) 19, a heating unit 21 and temperature sensor or temperature and pressure sensors 23. Fluid injection port 20 which is mounted on fluid outlet line 16 serves for increasing or decreasing the volume of the circulating fluid in the closed loop by enabling injection of fluid into the system while fluid is circulating therethrough and without exposing the circulated fluid to air or contaminants. Fluid injection port 20 is located on line 16 to enable regulated self delivery (through suction which its rate controlled by regulating a stopcock valve) of fluids (about 30-100 ml per minute) contained in a delivery syringe which is connected to port 20 without having to pressurize the syringe fluid (by means of a plunger).

As used herein the term "about" refers to ±10%.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of treating an overactive bladder or interstitial cystitis comprising:
   (a) delivering a first volume of a fluid maintained at a temperature of 40-48° C. directly into a urinary bladder of a subject having the overactive bladder or interstitial cystitis and circulating said volume of fluid within the urinary bladder;
   (b) gradually delivering a second volume of said fluid maintained at a temperature of 40-48° C. into said urinary bladder up to a predetermined fluid volume and/or pressure based on a tolerance of said subject to thereby relax detrusor muscles and stretch the urinary bladder; and
   (c) evacuating said fluid and urine from said urinary bladder.

2. The method of claim 1, wherein said predetermined fluid pressure is 30-60 cm of water.

3. The method of claim 1, wherein said circulating is effected using a closed loop system.

4. The method of claim 3, wherein (b) is effected by suctioning fluid into said closed loop system.

5. The method of claim 4, wherein said suctioning is effected while said fluid is circulating through said closed loop system.

6. The method of claim 1, wherein said predetermined fluid volume is in a range of 200 to 800 ml.

7. The method of claim 1, wherein (a) and (b) are effected via a catheter including one fluid conduit for inflating a positioning balloon and two additional fluid conduits for delivering and circulating said fluid.

* * * * *